US011806383B2

United States Patent
Cohen et al.

(10) Patent No.: US 11,806,383 B2
(45) Date of Patent: Nov. 7, 2023

(54) TOPICAL COMPOSITIONS COMPRISING PEA PROTEINS AND POLYPHENOLS

(71) Applicant: DEVINTEC SAGL, Lugano (IT)

(72) Inventors: Miguel Angel Alonso Cohen, Barcelona (ES); Marco Di Fulvio, Soriano Nel Cimino (IT)

(73) Assignee: DEVINTEC SAGL, Lugano (IT)

( * ) Notice: Subject to any disclaimer, the term of this patent is extended or adjusted under 35 U.S.C. 154(b) by 0 days.

(21) Appl. No.: 17/757,832

(22) PCT Filed: Dec. 21, 2020

(86) PCT No.: PCT/EP2020/087490
§ 371 (c)(1),
(2) Date: Jun. 22, 2022

(87) PCT Pub. No.: WO2021/130180
PCT Pub. Date: Jul. 1, 2021

(65) Prior Publication Data
US 2023/0042584 A1    Feb. 9, 2023

(30) Foreign Application Priority Data
Dec. 23, 2019    (IT) ................ 102019000025246

(51) Int. Cl.
| | | |
|---|---|---|
| *A61K 38/16* | (2006.01) | |
| *A61P 31/04* | (2006.01) | |
| *A61K 9/00* | (2006.01) | |
| *A61K 9/06* | (2006.01) | |
| *A61K 31/192* | (2006.01) | |
| *A61K 31/216* | (2006.01) | |
| *A61K 31/353* | (2006.01) | |
| *A61K 36/48* | (2006.01) | |
| *A61K 47/02* | (2006.01) | |
| *A61K 47/06* | (2006.01) | |
| *A61K 47/08* | (2006.01) | |
| *A61K 47/10* | (2017.01) | |
| *A61K 47/12* | (2006.01) | |
| *A61K 47/24* | (2006.01) | |
| *A61K 47/44* | (2017.01) | |

(52) U.S. Cl.
CPC .......... *A61K 38/168* (2013.01); *A61K 9/0014* (2013.01); *A61K 9/0034* (2013.01); *A61K 9/06* (2013.01); *A61K 31/192* (2013.01); *A61K 31/216* (2013.01); *A61K 31/353* (2013.01); *A61K 36/48* (2013.01); *A61K 47/02* (2013.01); *A61K 47/06* (2013.01); *A61K 47/08* (2013.01); *A61K 47/10* (2013.01); *A61K 47/12* (2013.01); *A61K 47/24* (2013.01); *A61K 47/44* (2013.01); *A61P 31/04* (2018.01)

(58) Field of Classification Search
CPC .. A61K 38/168; A61K 9/0014; A61K 9/0034; A61K 9/06; A61K 31/192; A61K 31/216; A61K 31/353; A61K 36/48; A61K 47/02; A61K 47/06; A61K 47/08; A61K 47/10; A61K 47/12; A61K 47/24; A61K 47/44; A61K 8/36; A61K 8/64; A61K 36/185; A61K 47/42; A61K 31/37; A61K 36/74; A61K 38/01; A61K 38/16; A61K 47/14; A61K 47/26; A61P 31/04; A61P 31/10; A61P 15/02; A61P 17/00; A61P 17/02; A61P 17/06; A61P 17/08; A61P 17/10; A61P 33/02; A61Q 19/00

See application file for complete search history.

(56) References Cited

U.S. PATENT DOCUMENTS

| | | | |
|---|---|---|---|
| 6,184,199 B1 | 2/2001 | Pauly | |
| 2008/0293826 A1* | 11/2008 | Rose | A61K 8/8158 514/762 |
| 2015/0094266 A1* | 4/2015 | Di Fulvio | A61K 31/732 514/13.2 |
| 2015/0238462 A1 | 8/2015 | Blanchard et al. | |
| 2017/0095528 A1 | 4/2017 | Alonso et al. | |
| 2017/0252366 A1* | 9/2017 | Cohen | A61K 31/80 |
| 2018/0318333 A1* | 11/2018 | Cohen | A61K 45/06 |
| 2019/0091288 A1* | 3/2019 | Alonso Cohen | A61K 36/48 |

FOREIGN PATENT DOCUMENTS

| | | | | |
|---|---|---|---|---|
| CN | 103622955 | * | 2/2014 | ............ A61P 31/10 |

OTHER PUBLICATIONS

Esposito et al. Effect of pea protein plus grape seed dry extract on a murine model of *Candida albicans* induced vaginitis. Future Microbiology, Sep. 26, 2018. vol. 13, No. 12, pp. 1375-1382. (Year: 2018).*
CN103622955 English machine translation obtained from patents.google.com, 19 pages. Date Feb. 2014. (Year: 2014).*
Fernandes de Araújo et al. Polyphenols and their applications: An approach in food chemistry and innovation potential. Food Chemistry, vol. 338 (2021)127535, pp. 1-15. (Year: 2021).*
Yilmaz et al. Major Flavonoids in Grape Seeds and Skins: Antioxidant Capacity of Catechin, Epicatechin, and Gallic Acid. J. Agric. Food Chem. 2004, vol. 52, pp. 255-260. (Year: 2004).*
Fahim J. R. et al., "The phenolic profile of pea (*Pisum sativum*): a phytochemical and pharmacological overview", Phytochem Rev, 18:173-198, Year: 2019.

(Continued)

*Primary Examiner* — Marcela M Cordero Garcia
(74) *Attorney, Agent, or Firm* — SILVIA SALVADORI, P.C.; Silvia Salvadori

(57) ABSTRACT

The object of the invention is topical compositions comprising pea proteins and polyphenols and the use thereof for the treatment of local or generalised disorders caused by increased permeation of the natural epithelial barriers. Said disorders may be of bacterial, viral, inflammatory, allergic and/or fungal origin, or endogenous or idiopathic.

9 Claims, 6 Drawing Sheets

(56) References Cited

OTHER PUBLICATIONS

International Preliminary Report on Patentability of PCT/EP2020/087490 dated Oct. 14, 2021.
Search Report and Written Opinion of PCT/EP2020/087490 dated Apr. 6, 2021.

* cited by examiner

A

ABSTRACT

TOPICAL COMPOSITIONS COMPRISING PEA PROTEINS AND POLYPHENOLS

This application is a U.S. national stage of PCT/EP2020/087490 filed on 21 Dec. 2020, which claims priority to and the benefit of Italian Patent Application No. 102019000025246 filed on 23 Dec. 2019, the contents of which are incorporated herein by reference in their entireties.

The object of the invention is topical compositions comprising pea proteins and polyphenols and the use thereof for the treatment of local or generalised disorders caused by increased permeation of the natural epithelial barriers. Said disorders may be of bacterial, viral, inflammatory, allergic and/or fungal origin, or endogenous or idiopathic.

PRIOR ART

Complexes of tannins with animal proteins, especially gelatin of bovine origin, albumin, casein or ovalbumin, have been proposed as effective remedies for gastrointestinal disorders.

The use of said complexes in the treatment of diarrhoea, for example, is disclosed in EP 1764105, EP 2526939, EP 2361623 and US 20090062191. Gelatin tannate has been available on the market for some time as a medical device for the treatment of acute diarrhoea.

As an alternative to the use of the tannin and animal protein complexes, the complex of proanthocyanidins with pea protein has been proposed (WO2014154796). Said complex is particularly effective in the treatment of disorders caused by alterations of the intestinal epithelial tissue (non-ciliated simple columnar epithelium).

WO2018167131 describes combinations and conjugated products of pea protein and polysaccharides, in particular xyloglucans, fucoidans and ulvans, for topical treatment of inflammatory skin disorders such as atopic dermatitis, psoriasis, rosacea and rashes.

DESCRIPTION OF THE INVENTION

Figure 1:
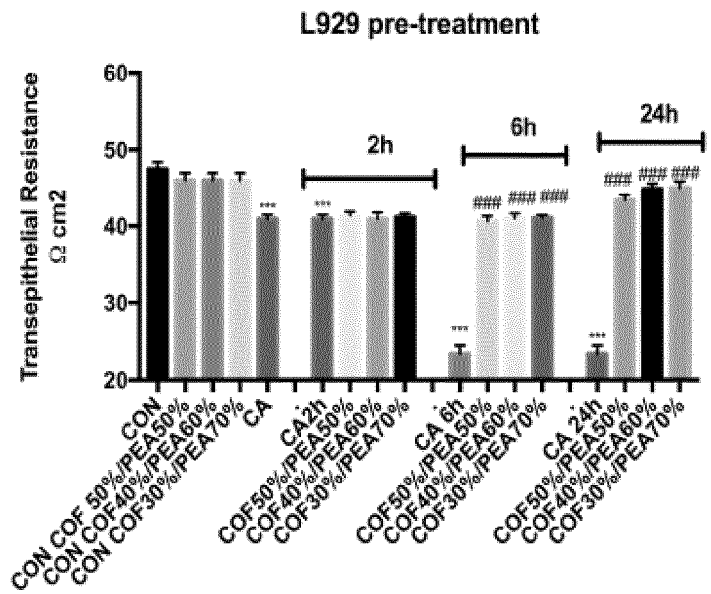
FIG. 1A shows that pre-treatment at various time with formulations 1-3 preserved the reduction in TEER induced by Candida.
FIG. 1B shows that pretreatment at various time with formulations 1-3 preserved the membrane integrity of fibroblasts infected with *S. aureus*.

It has now been found that the combination of pea protein and low-molecular-weight polyphenols belonging to the hydroxybenzoic and hydroxycinnamic acid families is particularly effective in the treatment of skin and mucosal disorders due to impairment of the barrier effect and of the intercellular tight junctions of the dermal and mucosal epithelia.

The invention therefore relates to topical formulations comprising combinations or complexes of pea protein with polyphenols belonging to the hydroxycinnamic and hydroxybenzoic acid families.

A further aspect of the invention relates to said combinations, complexes and formulations for use in the treatment of skin and mucosal disorders due to impairment of the barrier effect, and in particular in the treatment of local or generalised disorders caused by increased permeation of the natural epithelial barriers.

The formulations according to the invention exhibit increased specificity of action and optimum technological characteristics, which allow wide formulation flexibility.

The term "skin and mucosal disorders due to impairment of the barrier effect" is clear to the skilled person, as demonstrated, for example, by the following references: Grainne M. O. et al., "Filaggrin in atopic dermatitis", J. Allergy Clin. Immunol., 2008, vol. 122(4), 689-693; Dorota Purzycka-Bohdan et al., "Genetic background of skin barrier dysfunction in the pathogenesis of psoriasis vulgaris", Postepy Dermatol Allergol., 2015, 32(2), 123-126; and Flavia Alvim Sant'Anna Addor "Skin barrier in rosacea", Ann. Bras Dermatol., 2016, vol. 91 (1), 59-63.

Atopic dermatitis, psoriasis, rosacea, contact dermatitis, cutaneous candidiasis, fungal or bacterial infections are examples of disorders wherein the barrier effect of the skin is impaired. Vaginal candidiasis is an example of a disorder wherein the barrier effect of the mucosa is impaired.

The compositions according to the invention facilitate inhibition of the mechanisms whereby allergens, bacteria, viruses and fungi pass through the epithelia, by reducing the permeability of the tight junctions and inhibiting paracellular transport to other systems. The compositions of the invention also control and reduce water loss, with a consequent reduction in exposure to pro-allergenic factors.

The reinstatement of the barrier effect or prevention of its impairment obtainable with the formulations according to the invention also effectively counteract the transfer of the disorder from the epithelium to other systems, a phenomenon known as the "atopic march", described by Selene K. Bantz et al., "*The Atopic March: Progression from Atopic Dermatitis to Allergic Rhinitis and Asthma*" in J Clin Cell Immunol. 2014 April; 5(2): 202.

"Pea protein" here means a protein powder containing legumin obtained by extraction by known methods from Pisum sativum seeds. Pea protein is available on the market under the trademarks Nutralys®, Pisane® and P80X. Commercially available products can be obtained, for example, from Cosucra and Dal Cin Gildo S.p.a. The product presents as a yellowish powder with a characteristic odour, which is poorly soluble in water.

The polyphenols which can be used according to the invention belong to the class of hydroxycinnamic and hydroxybenzoic acids. Examples of said polyphenols comprise ferulic acid, isoferulic acid, chlorogenic acid, ellagic acid, gallic acid and rosmarinic acid, preferably ellagic acid and chlorogenic acid. The polyphenols can be present in a substantially pure, isolated form, or in the form of extracts containing them in percentages ranging from 10 to 80%, depending on the source.

A known source of ellagic acid, for example, is pomegranate extract, which has an ellagic acid content typically ranging between 30 and 60% by weight.

A known source of chlorogenic acid, for example, is green coffee extract, which has a chlorogenic acid content typically ranging between 35 and 65% by weight.

The weight ratio of polyphenol to pea proteins ranges between 0.4:1 and 1:10; the ratio preferably ranges from 1:1 to 1:6. The weight ratio of pea protein to an extract containing 40 to 50% by weight of polyphenol can range from 1:1 to 1:3, preferably 1:1.

Examples of suitable forms of administration comprise ointments, lotions, creams, solutions, suspensions, gels, mouthwashes, medicated patches or gauze, powders, pessaries and other forms suitable for topical application to the skin and mucosa.

The weight percentage of the pea protein can range from 1 to 30% of the total weight of the formulation, preferably from 1.5 to 10%, while the weight percentage of the polyphenol can range from 0.5 to 25% of the total weight of the formulation.

The formulations of the invention are prepared by known methods and with known carriers. The mixture of polyphenol and pea protein according to the invention is preferably associated with moisturising agents, emollients, humectants, preservatives, antioxidants and pH regulators. Examples of said agents are given in WO 2018/167131. Non-lipidic acidifiers such as lectin, lactic acid, sericin, poloxamers, carrageenan and arabinoxylan are particularly preferred. Of these, the following are particularly preferred: one or more of the following compounds selected from lectin, poloxamers, carrageenan and arabinoxylan, each at concentrations ranging from 0.1 to 2.5% by weight.

If desired, the formulations according to the invention can contain other active ingredients such as sucralfate, hyaluronic acid, antibiotics, steroidal and non-steroidal anti-inflammatories, chitosan, antihistamines and extracts of medicinal plants, in particular *Zanthoxylum bungeanum*, *Aloe vera* and camomile extracts.

The compositions according to the invention are particularly useful for the treatment of atopic dermatitis, rosacea, psoriasis, contact dermatitis, dermatitis caused by exposure to sunlight, radiotherapy or chemotherapy, cutaneous candidiasis, fungal infections, vaginal candidiasis, polybacterial vaginitis, fungal and bacterial infections of the skin and mucosa, and infections caused by protozoa.

The examples below illustrate the invention in greater detail.

EXAMPLE 1

Cream formulation for cutaneous application (percentages by weight)

| Ingredient | % |
| --- | --- |
| Pea protein | 1.5% |
| Ferulic acid | 1.5% |
| Sericin | 2% |
| *Zanthoxylum b.* extract | 0.5% |
| Lactic acid | 0.3% |
| Palmitate | 6% |
| Cocoa butter | 1% |
| Petrolatum | 1% |
| Dimethicone | 2% |
| Cetearyl alcohol | 3% |
| Propylene glycol | 1% |
| Glycerin | 1% |
| Disodium EDTA | 0.2% |
| Phenoxyethanol | 1% |
| Dicetylphosphate | 1% |
| Water | q.s. to 100 |

EXAMPLE 2

Cream formulation for cutaneous application (percentages by weight)

| Ingredient | % |
| --- | --- |
| Pea protein | 2.5% |
| Chlorogenic acid | 2.5% |
| Sericin | 2% |
| *Zanthoxylum b.* extract | 0.3% |
| Lectin | 1% |
| Palmitate | 6% |
| Cocoa butter | 1% |
| Petrolatum | 1% |
| Dimethicone | 2% |
| Cetearyl alcohol | 3% |
| Propylene glycol | 1% |
| Glycerin | 1% |
| Carrageenan | 1% |
| Disodium EDTA | 0.2% |
| Phenoxyethanol | 1% |
| Dicetylphosphate | 1% |
| Water | q.s. to 100 |

EXAMPLE 3

Cream formulation for vaginal application (percentages by weight)

| Ingredient | % |
| --- | --- |
| Pea protein | 2.5% |
| Ellagic acid | 2.5% |
| *Zanthoxylum b.* extract | 0.2% |
| Arabinoxylan | 2% |
| Lactic acid | 0.4% |
| Poloxamer | 2% |
| Sericin | 3% |
| Squalane | 2% |
| Sodium bicarbonate | 3% |
| Salcare ® | 4% |
| Nipaguard ® | 1% |
| Water | q.s. to 100 |

EXAMPLE 4

Cream formulation for vaginal application (percentages by weight)

| Ingredient | % |
| --- | --- |
| Pea protein | 2.5% |
| Gallic acid | 2.5% |

-continued

| Ingredient | % |
|---|---|
| Poloxamer | 5% |
| Zanthoxylum b. extract | 0.5% |
| Lactic acid | 0.4% |
| Poloxamer | 2% |
| Sericin | 3% |
| Sodium bicarbonate | 3% |
| Salcare ® | 4% |
| Nipaguard ® | 1% |
| Carrageenan | 1% |
| Water | q.s. to 100 |

EXAMPLE 5

Three cream formulations containing 5% by weight of the following mixtures:
1. 50% green coffee extract containing 45% chlorogenic acid and 50% pea protein;
2. 40% green coffee extract containing 45% chlorogenic acid and 60% pea protein;
3. 30% green coffee extract containing 45% chlorogenic acid and 70% pea protein,
were subjected to the permeability adhesion test (TEER) using murine fibroblasts L-929 which were infected with *Staphylococcus aureus* and *Candida albicans* strains.

Figure 1B:
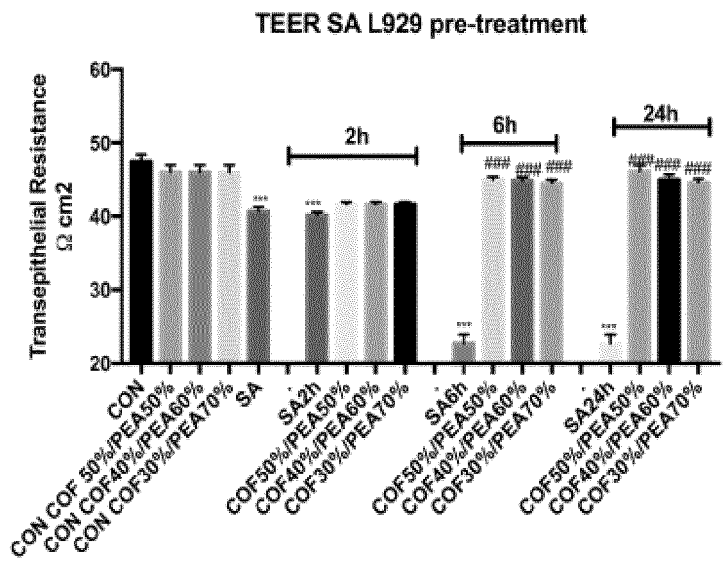

Pre-treatment at various times with formulations 1-3 preserved the reduction in TEER induced by *Candida* (FIG. 1A) and the membrane integrity of fibroblasts infected with *S. aureus* (FIG. 1B).

Figure 2A:
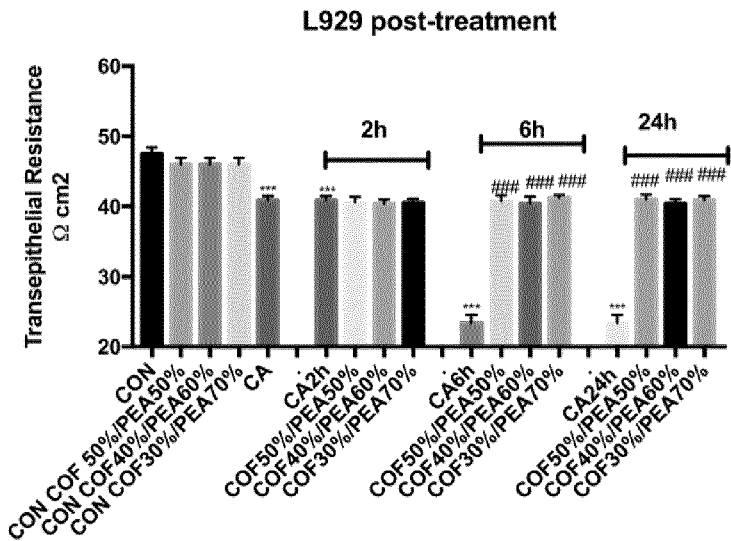
FIG. 2A shows that post-treatment increased TEER 6 and 24 hours after Candida infections.
Figure 2B:
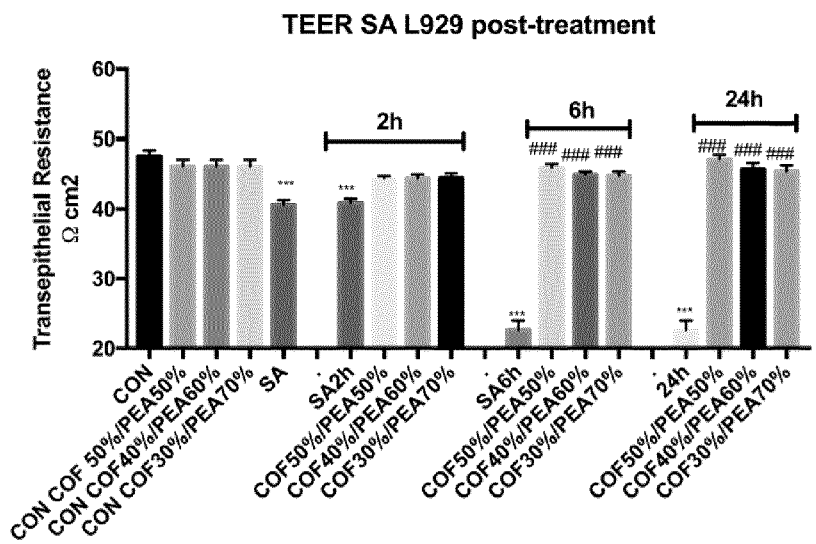
FIG. 2B shows that post-treatment preserved membrane integrity to a time dependent extent as from 6 hours after the *S. aureus* infection.

Post-treatment increased TEER 6 and 24 hours after the Candida infection (FIG. 2A) and preserved membrane integrity to a time-dependent extent as from 6 hours after the *S. aureus* infection (FIG. 2B).

Figure 3A:
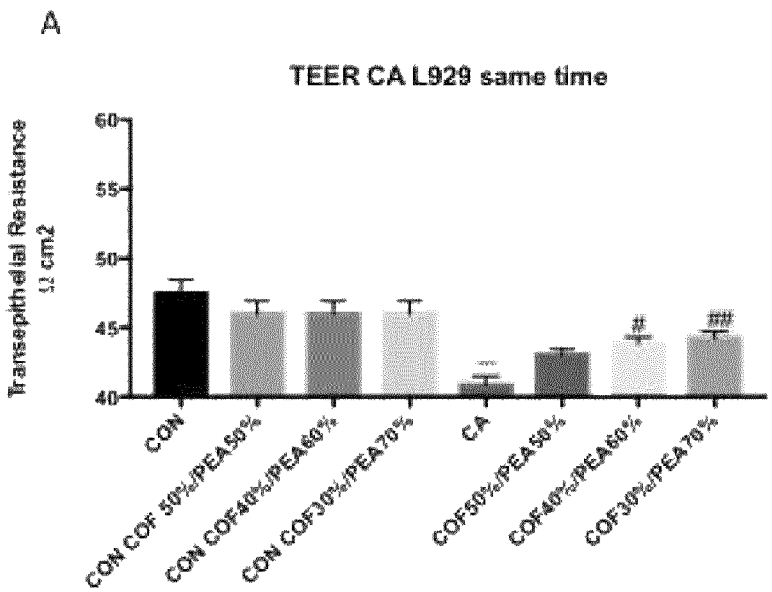
FIG. 3A shows loss of membrane integrity in fibroblast infected by Candida when the mixtures were administered simultaneously with the infection.
Figure 3B:
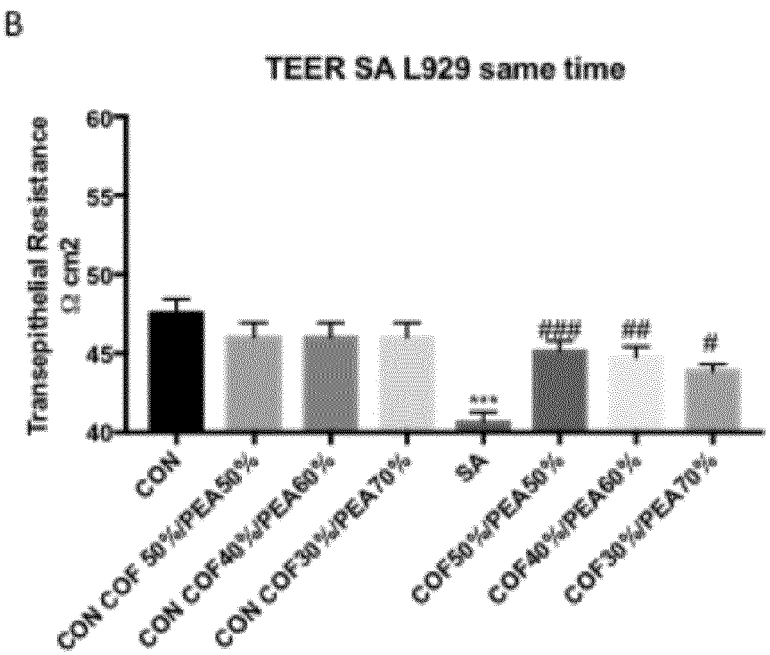
FIG. 3B shows limited increased TEER in fibroblast infected by *S. aureus* when the mixtures were administered simultaneous with the infection.

When the mixtures were administered simultaneously with the infection, loss of membrane integrity (FIG. 3A) in fibroblasts infected by *Candida,* and increased TEER in fibroblasts infected by *S. aureus* (FIG. 3B), were again limited.

EXAMPLE 6

Three cream formulations containing 5% by weight of the following mixtures:
1. 50% pomegranate extract containing 40% ellagic acid and 50% pea protein;
2. 40% pomegranate extract containing 40% ellagic acid and 60% pea protein;
3. 30% pomegranate extract containing 40% ellagic acid and 70% pea protein,
were subjected to the permeability adhesion test (TEER) using a vaginal epithelium cell line VK2 E6/E7 (ATCC CRL-2616) which was infected with *Gardnerella vaginalis* (GV) and *Candida albicans* (CA) strains.

Figure 4A:
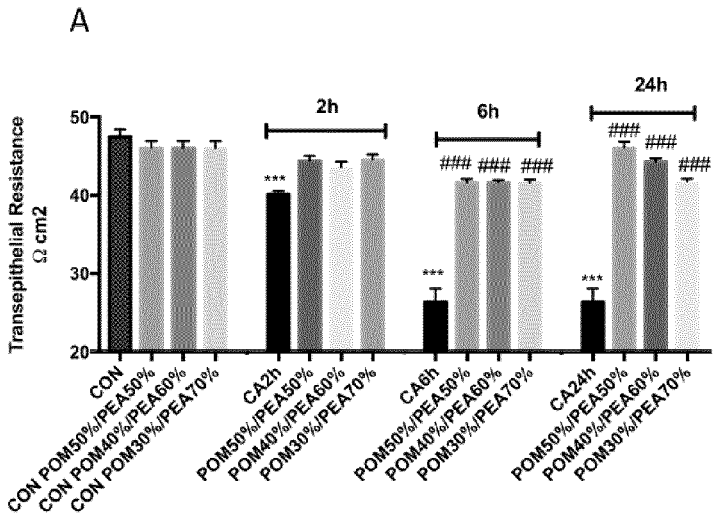
FIG. 4A shows that pre-treatment at various time with formulations 1-3 preserved the membrane properties against Candida infection.
Figure 4B:
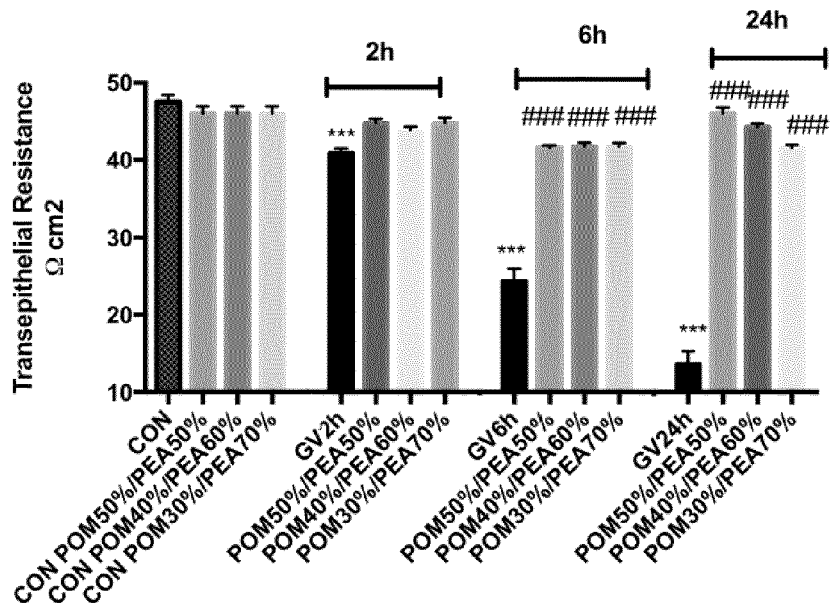
FIG. 4B shows that pre-treatment at various time with formulations 1-3 preserved the membrane properties against *Gardnerella vaginalis* infection.

Pre-treatment at various times with formulations 1-3 preserved the membrane properties against CA and GV infection (FIGS. 4A and 4B).

Figure 5A:
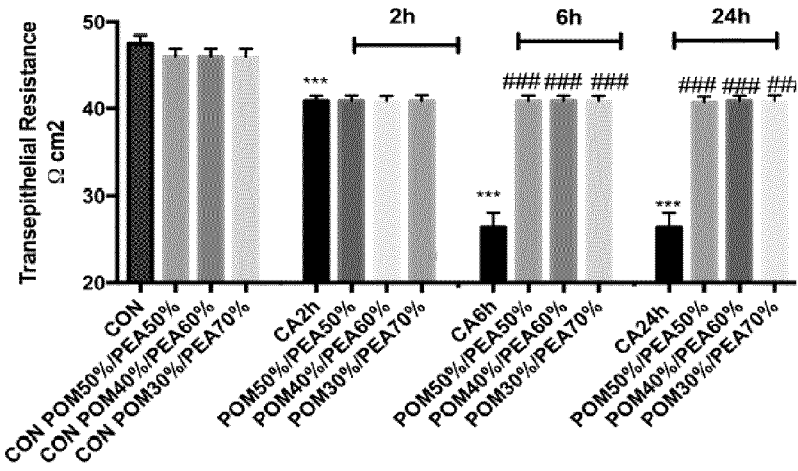
FIG. 5A shows that post-treatment preserved membrane integrity at 6 hours after Candida infection.
Figure 5B:
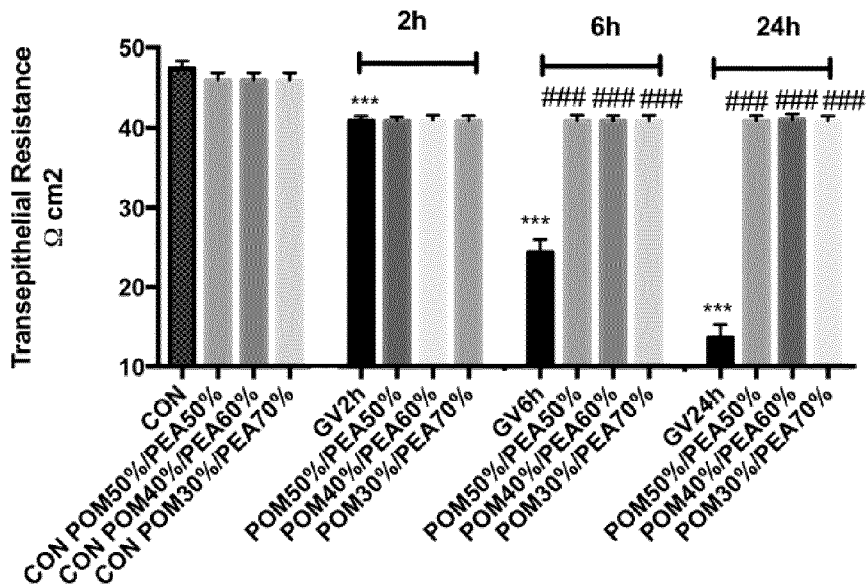
FIG. 5B shows that post-treatment preserved membrane integrity 24 hours after Candida infection.

Post-treatment preserved membrane integrity 6 and 24 hours after *Candida* infection (FIG. 5A and 5B).

Figure 6A:
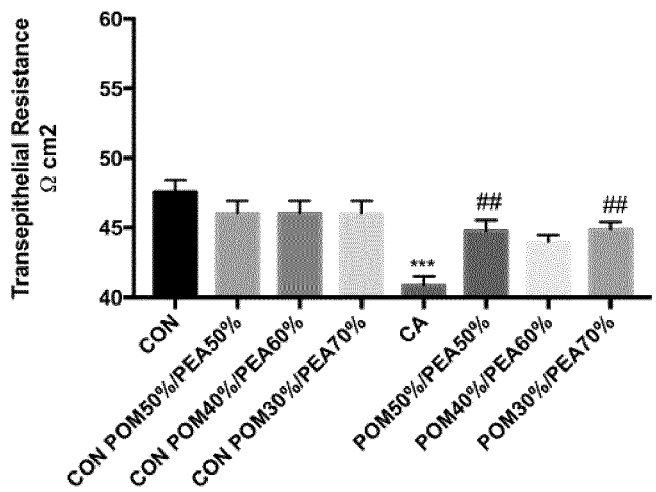
FIGS. 6A and 6B show that when the mixtures were administered simultaneously with the infection, TEER increased in the infected cells.
Figure 6B:
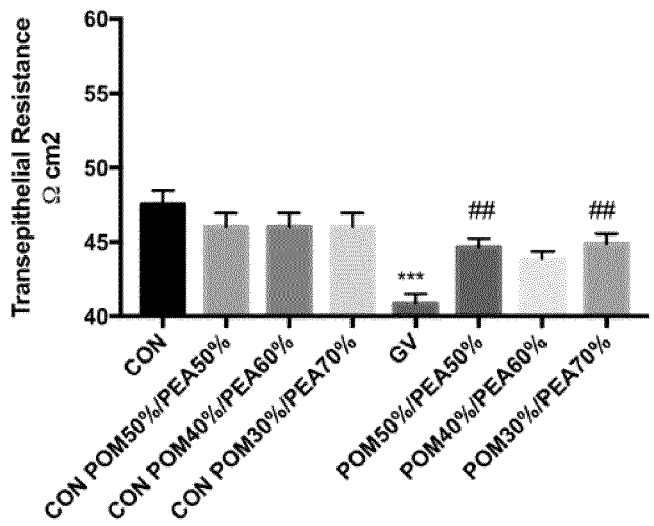

When the mixtures were administered simultaneously with the infection, TEER increased in the infected cells (FIG. 6A and 6B).

The invention claimed is:
1. Method of treating localized disorders of bacterial, viral, inflammatory, allergic and/or fungal, endogenous, or idiopathic origin caused by permeation of the natural epithelial barriers, and disorders transferred from the epithelia to other systems in a subject in need thereof, said method comprising
administering a pharmaceutically effective amount of topical compositions comprising pea protein and polyphenols of the hydroxycinnamic and hydroxybenzoic acid families wherein the weight ratio of polyphenol to pea protein is from 0.4:1 to 1:10, in admixture with a suitable carrier to said subject, wherein the polyphenols are selected from chlorogenic acid and ellagic acid.
2. The method according to claim 1, wherein said localized disorders comprise atopic dermatitis, rosacea, psoriasis, contact dermatitis, dermatitis caused by exposure to sunlight, radiotherapy or chemotherapy, cutaneous candidiasis, fungal infections, vaginal candidiasis, polybacterial vaginitis, fungal and bacterial infections of the skin and mucous membranes, and infections caused by protozoa.
3. The method according to claim 1, wherein the polyphenol is ellagic acid.
4. The method according to claim 1, wherein the weight ratio of polyphenol to pea protein ranges from 1:1 to 1:6.
5. The method according to claim 1, wherein the weight ratio of polyphenol to pea protein is 1:1.
6. The method according to claim 1, wherein the compositions are in the form of ointments, lotions, creams, solutions, suspensions, gels, mouthwashes, medicated plasters or gauzes, powders, or pessaries.
7. The method according to claim 1, wherein the compositions further comprise moisturising, emollient, humectant, preservative, antioxidant, or pH-regulating additives.
8. The method according to claim 7, wherein the additives are selected from lectin, lactic acid, sericin, poloxamers, carrageenan and arabinoxylan.
9. The method according to claim 8, wherein the additives are selected from lectin, poloxamers, carrageenan and arabinoxylan, each in concentrations by weight ranging from 0.1 to 2.5%.

* * * * *